United States Patent
Coats et al.

(10) Patent No.: US 10,500,026 B2
(45) Date of Patent: Dec. 10, 2019

(54) DISPENSER

(71) Applicant: AAN MEDICAL LIMITED, Salisbury (GB)

(72) Inventors: Andrew Coats, Salisbury (GB); Nigel Davis, Welwyn Garden (GB); Andrew Tulloch, Berkshire (GB)

(73) Assignee: AAN MEDICAL LIMITED, Salisbury (GB)

( * ) Notice: Subject to any disclaimer, the term of this patent is extended or adjusted under 35 U.S.C. 154(b) by 601 days.

(21) Appl. No.: 15/046,755

(22) Filed: Feb. 18, 2016

(65) Prior Publication Data
US 2016/0158465 A1 Jun. 9, 2016

Related U.S. Application Data

(63) Continuation-in-part of application No. PCT/GB2014/052589, filed on Aug. 26, 2014.

(30) Foreign Application Priority Data

Aug. 30, 2013 (GB) .................................. 1315529.6
Feb. 19, 2015 (GB) .................................. 1502822.8
Mar. 26, 2015 (GB) .................................. 1505095.8

(51) Int. Cl.
*A61D 7/00* (2006.01)
*A61M 11/00* (2006.01)
*B05B 11/00* (2006.01)

(52) U.S. Cl.
CPC .............. *A61D 7/00* (2013.01); *A61M 11/00* (2013.01); *A61M 11/006* (2014.02); *B05B 11/00* (2013.01);
(Continued)

(58) Field of Classification Search
CPC .............. A61M 11/006; A61M 11/00; A61M 2205/13; A61M 2210/083;
(Continued)

(56) References Cited

U.S. PATENT DOCUMENTS

| 1,089,595 | A | 3/1914 | Sopha |
| 4,670,010 | A | 6/1987 | Dragone |

(Continued)

FOREIGN PATENT DOCUMENTS

| EP | 0 810 003 A2 | 12/1997 |
| FR | 2885507 | 11/2006 |

(Continued)

OTHER PUBLICATIONS

International Search Report for PCT/GB2014/052589 dated Dec. 15, 2014, three pages.
(Continued)

*Primary Examiner* — Adam Marcetich
*Assistant Examiner* — Jessica R Arble
(74) *Attorney, Agent, or Firm* — Nixon & Vanderhye P.C.

(57) ABSTRACT

A drug or medical treatment dispenser comprises a hoop or a pair of semi-circular arms pivotally mounted together. The dispenser comprises at least one tube which is connected at one end to a pump. The pump is in turn connected to a replaceable container of treatment. The tube comprises one or more apertures to dispense treatment in spray form towards a body part of a person or animal which is placed within the dispenser.

14 Claims, 6 Drawing Sheets

(52) U.S. Cl.
CPC ..... *A61M 2205/13* (2013.01); *A61M 2205/18* (2013.01); *A61M 2205/3306* (2013.01); *A61M 2205/3375* (2013.01); *A61M 2205/3553* (2013.01); *A61M 2205/50* (2013.01); *A61M 2205/52* (2013.01); *A61M 2205/6009* (2013.01); *A61M 2205/6018* (2013.01); *A61M 2205/6072* (2013.01); *A61M 2205/8206* (2013.01); *A61M 2210/083* (2013.01); *A61M 2210/086* (2013.01)

(58) Field of Classification Search
CPC .......... A61M 2210/086; A61M 35/003; A61M 2210/04; A61M 35/00; B05B 11/00
See application file for complete search history.

(56) References Cited

U.S. PATENT DOCUMENTS

| | | | | |
|---|---|---|---|---|
| 5,148,556 | A * | 9/1992 | Bottoms, Jr. | .......... A47K 3/281 239/273 |
| 5,205,306 | A * | 4/1993 | Peterson | ................ A47K 3/287 134/104.2 |
| 2002/0082547 | A1* | 6/2002 | Deniega | ............ A61M 25/0043 604/48 |
| 2005/0008577 | A1 | 1/2005 | Cooper et al. | |
| 2005/0210576 | A1 | 9/2005 | Guerin et al. | |
| 2006/0025716 | A1 | 2/2006 | Babaev | |
| 2007/0186923 | A1 | 8/2007 | Poutiatine et al. | |
| 2009/0259204 | A1* | 10/2009 | Galdeti | ................ A61F 9/0026 604/302 |
| 2010/0312201 | A1* | 12/2010 | Hoege | .................... A61M 11/00 604/293 |
| 2011/0130745 | A1* | 6/2011 | Shevgoor | ................ A61M 5/14 604/523 |
| 2011/0174348 | A1 | 7/2011 | Helenius | |
| 2011/0203047 | A1 | 8/2011 | Jewett et al. | |
| 2012/0111971 | A1* | 5/2012 | Chang | ....................... F24H 1/06 239/128 |
| 2012/0267396 | A1* | 10/2012 | Quinlan, Jr. | ............. A47K 5/14 222/190 |
| 2014/0316370 | A1* | 10/2014 | Mernoe | ................ A61M 5/1411 604/500 |

FOREIGN PATENT DOCUMENTS

| | | |
|---|---|---|
| GB | 2 431 352 | 4/2007 |
| WO | WO 2011/073796 A2 | 6/2011 |
| WO | WO 2012/043075 | 4/2012 |
| WO | WO 2013/114096 | 8/2013 |
| WO | 2013/139588 A1 | 9/2013 |

OTHER PUBLICATIONS

JP Notice of Reasons for Rejection and English translation dated Jul. 3, 2018 in JP Application 2016-537378.

* cited by examiner

DISPENSER

CROSS-REFERENCES TO RELATED APPLICATIONS

This application is a Continuation-in-Part of:
International Application No. PCT/GB2014/052589 filed in English on 26 Aug. 2014 claiming priority to GB Applications No GB1315529.6 filed 30 Aug. 2013;
GB Application No. GB1502822.8 filed 19 Feb. 2015; and
GB Application No. GB1505095.8 filed 26 Mar. 2015.
The entire contents of these applications are incorporated herein by reference.

FIELD OF THE INVENTION

This invention relates to dispensers for delivering doses of pharmaceuticals and other medical treatments to people. Although designed originally for humans, it can also be applied to animals, and is particularly effective in treating domestic and farm animals.

BACKGROUND ART

Provision of drugs and other medical treatments has been usually by injection, pills, and nasal sprays; more recently transdermal patches have been used to deliver a measured amount of the drug or other treatment concerned. In this specification "treatment" includes pre-treatments of persons to minimise their risk of reaction if subsequently exposed, for example, to hazardous gases.

There remains, however, an issue in ensuring the accuracy of delivery of the drug or other treatment concerned in some circumstances. In the case of transdermal treatments with patches, it is difficult to ensure the patch continues to adhere sufficiently to enable the drug or other treatment to cross the skin barrier for a long enough time for the treatment to be effective.

A small number of drugs are available in spray-on formulations, but these require significant dexterity to apply and give very inconsistent doses due to variation in the accuracy of the user, the distance of the spray from the target and the number of times and force with which the nozzle is pressed.

DISCLOSURE OF THE INVENTION

According to the present invention a drug or medical treatment dispenser comprising a tube having a plurality of apertures to dispense treatment in spray form towards the skin of a person or animal and a container containing the drug or other medical treatment.

In one embodiment the drug or medical treatment dispenser comprises one or more tubes mounted in a hoop, the tubes having a plurality of apertures are disposed around the inside of the hoop and directing treatment emerging from the tubes towards a body part placed within the hoop.

In one arrangement of such an embodiment, the drug or medical treatment dispenser has a pair of tubes in which one of the pair of tubes is placed in one half of the hoop and the other of the pair is placed in the other half of the hoop.

In such a case the tubes may be closed at one of their ends. The tubes may be inset into grooves in the hoop.

In another embodiment the hoop is formed as two arms, the arms each having a proximal end and a distal end, the proximal ends of the arms are mounted on a pivot with a pair of tubes one mounted in each arm. The tubes at the proximal end of the arms are connected to the outlet of a pump and at each of the distal ends terminate with a nozzle, the nozzles directing treatment to a body part placed between the nozzles.

Normally, but not essentially a spring tends to urge the distal ends of the arms to butt together.

In addition to the nozzles, the tubes may have a plurality of apertures disposed around the inside of the hoop and directing treatment emerging from the tubes towards a body part placed within the hoop.

The apertures may comprise plain holes, self-sealable slits or nozzles.

The treatment is pumped into the tubes from a pump connected directly or indirectly to a container containing the treatment. The pump may be manually operated or electrically powered. Conveniently the hoop is mounted on a base and the pump in the base. Additionally if the pump is electrically driven a programmable chip may be incorporated in the circuit to control the times of treatment, and to measure other parameters of the treatment.

For field use dispenser the base is hand held, but otherwise it would normally be table mounted. For field use the dispenser may be in the form of a wand which is passed over a body part.

The invention enables the creation of a hospital or home-based device in one instance or an ambulance or battlefield device in another which can be passed over a wound and sprays on antiseptic, wound sealer etc., without the need for touch thus much reducing or eliminating the risk of cross infection.

The drug or other treatment container is normally a replaceable container containing the drug or other medical treatment. Arthritis drugs, analgesic, anti-inflammatory drug, wound sealant, antiseptic might be typical treatments administered with this invention. More than one container may be provided containing a series of treatments appropriate to a patient, the containers being opened and closed selectively as the treatment progresses.

In one embodiment involving replaceable containers, the containers are coded with a coding unique to the treatment. The coding is used by the dispenser to control the time and/or length of the treatment and/or the pressure of the treatment in the tube(s).

BRIEF DESCRIPTION OF DRAWINGS

In order that the invention may be more fully understood, examples of the invention of the invention are illustrated in the accompanying drawings in which.

DETAILED DESCRIPTION OF SOME EXAMPLES OF THE INVENTION

Figure 1:
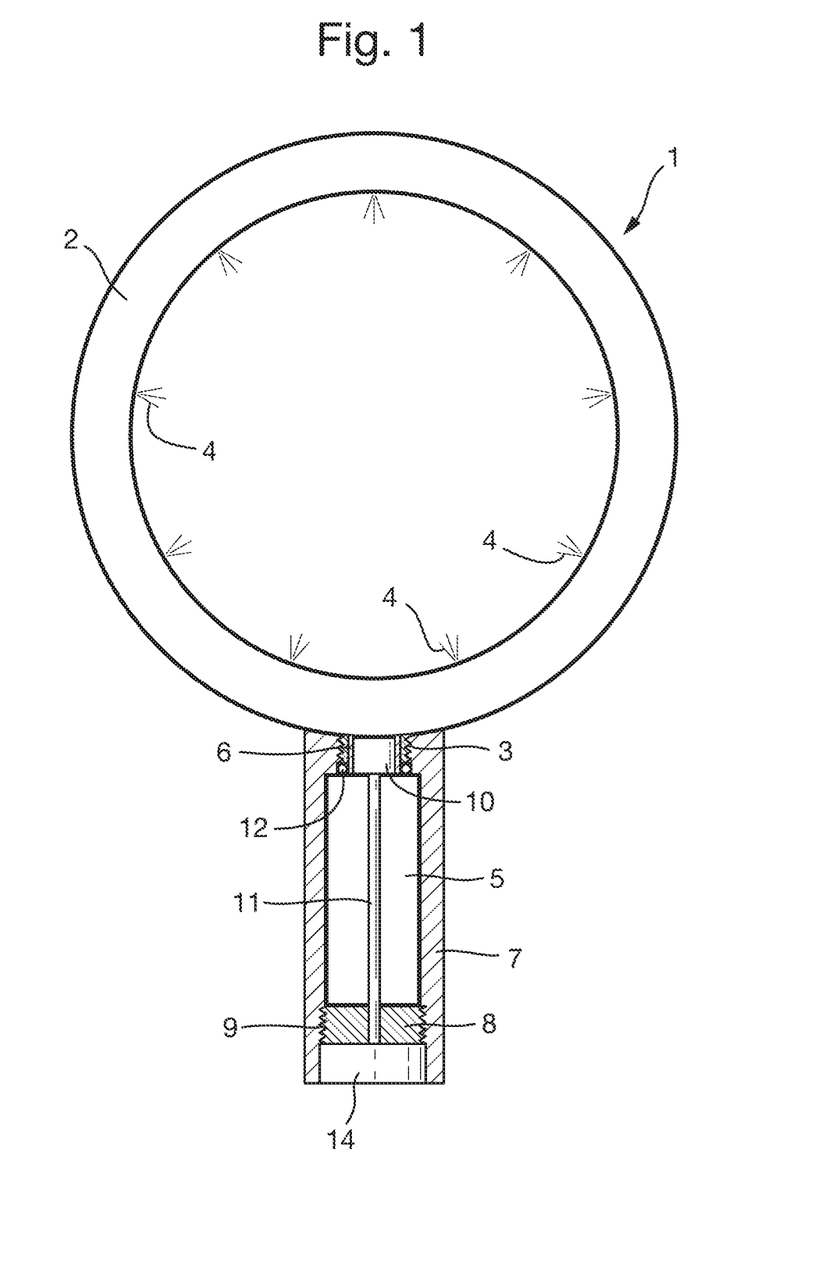
FIG. 1 illustrates a schematic side view in partial section a simple dispenser according to the invention.

FIG. 1 shows a drug or medical treatment dispenser 1 as comprising a continuous hollow hoop 2 having a plurality of inwardly directed apertures in the form of spray nozzles 4 which may be directed towards the skin of a person, joined to a container 5 containing the drug or other medical treatment is placed. Any spray emerging from nozzles 4 would fall on anything placed within the hoop. In practice this would be a finger, toe, arm or leg, or some other limb of a body of a person or animal.

The diameter of the hoop 2 is determined by the part of the body which it is intended to treat.

The hoop 2 in this case is a continuous loop with a junction 3 to a tube 6 connected to a container 5.

The spray nozzles 4 can be covered or closed selectively to allow for particular spray patterns to be imparted.

The container 5 is mounted within a handle 7 which is screwed to the outside of junction 3. The end of container 5 opposite tube 6 has a cap 8 sealed to the container 5, and has an external thread 9 enabling the container to be screwed into handle 7. The tube 6 is sealed against junction 3 with an O-ring seal 12.

A plunger 10 within tube 6 is connected to rod 11 extending through the container 5 to an actuator 14 within cap 8. A drug or any other treatment in container 5 is under pressure from a propellant, such than when actuator 14 moves rod 11 away from junction 3, the plunger 10 releases the content of the container into hoop 2 and thus through nozzles 4 onto anything within the hoop 2.

Container 5 is replaceable.

In one arrangement the container can be compartmented lengthways with different treatments in different compartments, each with their own plunger 10 and control rod 11 to open and close the compartments to junction 3.

Alternatively a plurality of junctions 3 can be provided each joined separately to a container and each container containing a separate treatment.

The dispenser shown in FIG. 1 may be hand held or mounted in a stand.

In FIGS. 2 to 5, a dispenser 20 according to the invention for spraying a fluid onto a body part comprises a hoop 21 and apertures 28 from which the fluid may be sprayed onto a body part within the hoop. A fluid connection 37 connects a container 32 mounted in receiver 55 and containing the fluid through an upstanding nipple 34 to the inlet 40 of a pump 31. The pump 31 has an outlet 33 which is connected a manifold 25. A pair of tubes 23 extends around internal groves 22 in the hoop 21. and have apertures 28 directed into the middle of the hoop 21. In a preferred arrangement, the apertures 28A, 28B, 28C, 28D increase in size as distance from the pump 31 increases so that the flow rate of the fluid from each aperture is substantially the same.

Figure 2:
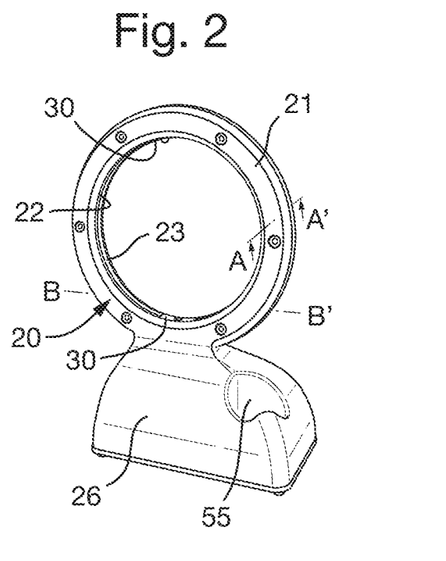
FIGS. 2 and 3 show perspective views of another example of a dispenser according to the invention.
Figure 3:
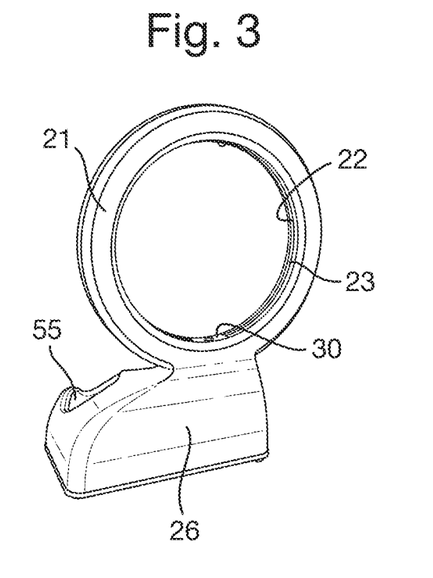
Figure 4:
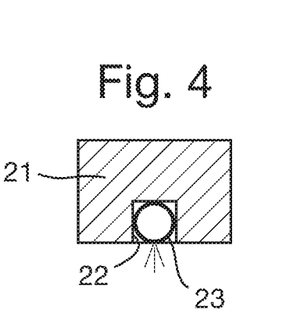
FIG. 4 is a section on the line A-A' of FIG. 2.
Figure 5:
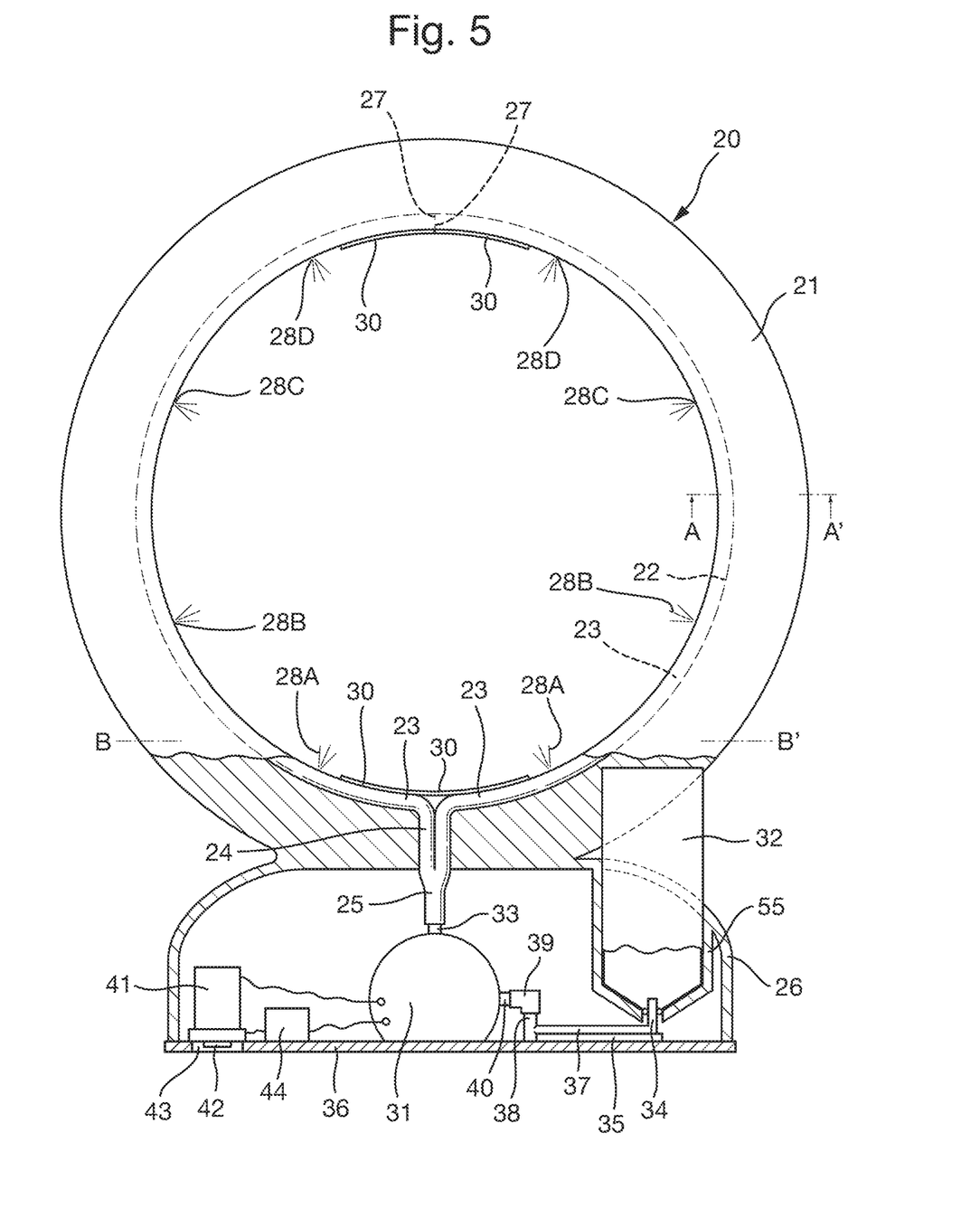
FIG. 5 is a schematic view of the dispenser of FIGS. 2 and 3 partially sectioned on the line B-B' of FIG. 1A.

For medical purposes, the tubes 23 comprise silicon rubber or like material suitable for medical use. Separate tubes 23 extended around the inside of the left-hand side of the hoop 21 and the right-hand side of the hoop 21 as seen in FIG. 2. The manifold 25 is mounted in a hollow base 26; the other ends 27 of the tubes are closed. The apertures 28A, 28B, 28C 28D are in the form of self-sealing slits increasing in size as one travels away from the pump 31 and manifold 25. The hoop 21 is mounted on the base 26. The tubes 23 are held in place at the top and bottom of the hoop 21 by plates 30.

A container 32 containing a fluid of interest is inserted through the top of the base 26 into a container receiver 55, with its outlet nozzle connected to the upstanding nipple 34 on a container mounting 35. The bottom of the base 26 is closed by a base plate 36. The container mounting 35 is mounted on the base plate 36. A fluid connection 37 is provided in the container base to a pump connector 38 also upstanding from the container mounting 35. A short length of tube 39 of silicon rubber or other suitable material connects the pump connector 38 to the pump inlet 40.

Container 32 is replaceable and may be subdivided to provide two or more different treatments.

The pump 31 is powered from a battery or mains source 41. In most cases the pump 31 would be triggered by a sensor (for example a sensor 53 as discussed with reference to FIGS. 5 and 6 below), although a switch 42 operated through an aperture 43 in the base plate can be used to turn the dispenser on and off. However, the switch in some arrangements may more conveniently be placed on the side of the base or isolated from user intervention altogether within the case. Optionally the aperture 43 may house a flexible rubber cover which allows the switch or other activation device 42 to be operated but which keeps dirt and moisture away from the inside of the base. If the switch is not intended for user operation and is inside the case, the aperture 43 would be omitted altogether. A programmable chip 44 can be set to limit the length of time during which the pump s switched on and/or to prevent operation of the pump 31 for a pre-set period following its previous operation. The programmable chip may also be programmed to vary the pump pressure (and thus the density and spread of any spray ejected through the apertures 28A, 28B, 28C, 28D).

In operation, a patient places a part of the body, say, an arm, wrist, hand, leg, ankle, foot etc., within the hoop 21. When the pump is activated by turning on the switch or operation of some other suitable activation device 42, a treatment contained in container 32 is pumped by pump 31 into each of the tubes 23 around the hoop 21. The pump pressure in the tubes 23 forces the fluid through the self-sealing slits 28 as a spray onto the patient's body part being treated.

In the device of FIGS. 2 to 5, the size of the part to be treated is limited by the diameter of the hoop 21.

Figure 6:
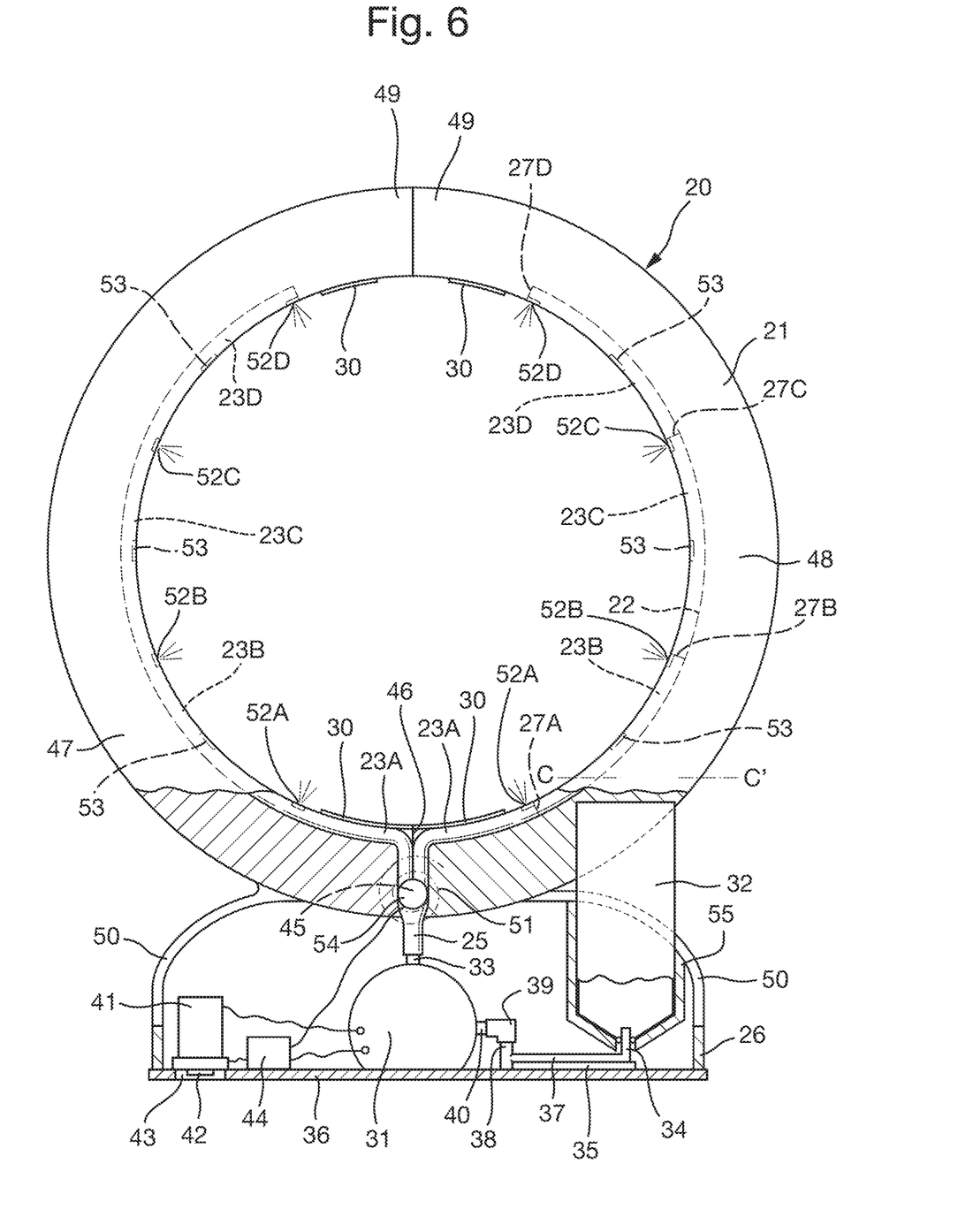
FIG. 6 is similar to FIG. 5 but illustrates a further development of the dispenser shown in FIGS. 2 to 5.
Figure 7:
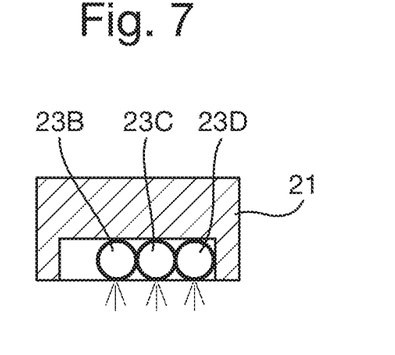
FIG. 7 is a section on the line C-C' of FIG. 6.

The device in FIGS. 6 and 7 overcomes this restriction. In FIGS. 6 and 7 the dispenser 20 comprises two semi-circular arms 47 and 48 pivoted at pivot 45 together at their lower proximal ends, and in the closed position butting against one another at their distal ends 49. The pivot 45 is mounted in a base 26 which has a slot 50 to enable the arms 47 and 48 to open and close. Optionally there is a spring 51 associated with the pivot 45, urging the arms to close together at the distal ends 49. As shown in FIGS. 6 and 7, when closed together the two semi-circulars arms 47 and 48 forms a hoop 21, however the two arms 47 and 48 could form a C or U shape rather than a hoop.

A fluid connection 37 connects to a container containing a fluid to be sprayed to the inlet of a pump 31. The pump 31 has an outlet 33 to which is connected a manifold 25. A plurality of tubes, 23A, 23B, 23C, 23D connect through sleeves 24 from the manifold 25 to the apertures 52A, 52B, 52C 52D distributed around the inside of the arms 47 and 48. The tubes 23A, 23B 23C and 23D are mounted in grooves 22 in the inner surfaces of the arms 47 and 48. Each individual tube 23A, 23B, 23C 23D connects an individual aperture 52A, 52B 52C and 52D to the manifold 25. In this arrangement, because the fluid pressure at each nozzle is substantially the same, the flow rate of the fluid from one aperture is substantially the same as that from another aperture. The ends 27A, 27B, 27C, 27D of the tubes 23 terminate with nozzles 52A, 52B, 52C, 52D which form the apertures. Self-sealing slits could replace the nozzles in this and other examples.

In the arrangement of FIGS. 6 and 7, the arms 47 and 48 are opened and a body part inserted between their distal ends 49. The body part can be substantially larger, such a thigh, chest or shoulder than could be inserted in hoop 21 of FIGS. 1 to 5. When the dispenser is ready to operate a container 32 containing a fluid of interest is inserted though the top of the base 26, into a container receiver 55, with its outlet nozzle connected to the upstanding nipple 34 on a container mounting 35. The bottom of the base 26 is closed by a base plate 36. The container mounting 35 is mounted on the base plate 36. A fluid connection 37 is provided in the container base from the container mounting 35 to pipe fluid a pump connector 38, also upstanding from the container mounting 35. A short length of tube 39 of silicon rubber or other suitable material connects the pump connector 38 to the pump inlet 40. The pump 31 has an outlet 33 to which is connected the manifold 25. Tubes 23A, 23B, 23C, 23D connect the manifold 25 individually to a nozzle 52A, 52B, 52C, 52D.

In the example of FIGS. 6 and 7, operation of the pump is controlled by a programmable chip 44 connected to a battery and a sensor 53 to detect when a body part has been inserted. The chip may be programmed to operate only at particular times of day, and/or after a particular time interval has elapsed from a previous treatment to prevent an overdose, and/or when a container with a particular bar code, which is read by a bar-code reader is mounted on nipple 34. However, in more sophisticated models, a series of sensors 53 is distributed around the inner surfaces of the arms 47 and 48 (sensors of this kind can also be distributed around the inside of hoop 21 in FIGS. 2 to 5). The sensors can detect the presence of a body part and in conjunction with the programmable chip 44, the sensors allow operation of the pump only when the correct body part is present, within the area bounded by arms 47 and 48 and hoop 21. The sensors in combination with the programmable chip can also identify the orientation of the body part. The chip 44 is connected in this configuration to motorised valves 54 controlling entry to tubes 23A, 23B 23C and 23D, in this way the direction of spraying can be controlled to ensure only that part of the body part to be sprayed is sprayed.

As before, the pump (and chip 44) is powered from a battery or mains source 41 through a switch 42. If it is to be available for user operation, the switch 42 can be operated through an aperture 43 in the base plate. However, the switch in some arrangements may more conveniently be placed on the side of the base. Optionally the aperture 43 may house a flexible rubber cover which allows the switch 42 to be operated but which keeps dirt and moisture away from the inside of the base. In other instances, user operation of the switch 42 is prevented and there is no external access to it. For clarity, connections between the sensors 53 and chip 44 are omitted. The programming of chip 44 follows standard practices in the field of image recognition.

The skilled person will be able readily to identify possible alternative configurations for the container mounting and/or pump for this invention. The hoops or arms need not be circular, but could be or semi-circular, square, elliptical or any other suitable shape.

The chip 44 not only enables control of the spray, but for medical purposes recording, for example, of the times of treatment, to enable medical professionals to monitor whether the patient is regularly undertaking the treatments. The chip 44 could also set off a reminder or an alarm if a pre-programmed treatment is missed, for example. The alarm can be local to the patient, or remote at control centre, a medical centre or hospital. The chip can be programmed to dispense different amounts of treatment to different patients or to operate different treatment regimes for different patients; the patient being identified by use of different switches, or input codes or other recognition system. An IR lamp and detector, other motion sensor, may be incorporated to prevent the system from operating unless a body part was present in the hoop, or between the distal ends of the arms 47 and 48 of FIGS. 6 and 7.

In the drawings, a battery 41 is used, this could be a long life conventional battery or a rechargeable battery such as an Li-ion battery; or the battery replaced by a mains supply stepped down to a safe voltage by a transformer, with a rechargeable battery back-up—for many domestic applications this may be the preferred option as it avoids loss of power as a result of batteries being discharged. For field operations this would not be practicable and battery power would be used.

In the examples, apertures in the form of both nozzles and self-sealing slits have been described and these can be interchanged in the examples.

The multi-tube approach of FIGS. 6 and 7 can be used with the closed hoop device of FIGS. 2 to 5.

In a further arrangement of the examples of FIGS. 2 to 7 the tubes can be of different diameters. In a still further arrangement, rather than using multiple tubes, a single tubes, whose diameter changes as it passes through each arm 47 and 48 in FIGS. 6 and 7 or each side of the hoop 21 in FIGS. 2 to 5 can be used instead to similar effect.

As a further development rather than using separate tubes 23, 23A, 23B, 23C, 23D, the tubes can be moulded as part of a moulding for the hoop 21 of FIGS. 1 to 5 or the arms 47 and 48 in the devices of FIGS. 6 and 7.

Examples of applications of the device include spray treatments of arthritis, burns, venous ulcers, chronic wounds/infections, eczema and other exfoliating conditions, and in trauma, eradication of MRSA from patients and ward staff/visitors, and disinfection. It can also be used for spray on wound sealing and dressings. A particular use is in treatment or applying temporary spray on dressings to patients in emergency evacuations.

In the configuration of FIGS. 2 to 7 the dispenser may comprise a plurality of hoops e.g. hand and finger sized, with sensors to determine which one to activate.

The sensors 53 could be IR, ultrasonic or other, some of which could give distance and/or orientation information. For example, if a hand is inserted off-centre, the device could adjust the sprays accordingly.

It is possible, if pressurised containers are used, a container outlet can be coupled directly to manifold 25 with the pump 31 and its control systems omitted.

Figure 8:
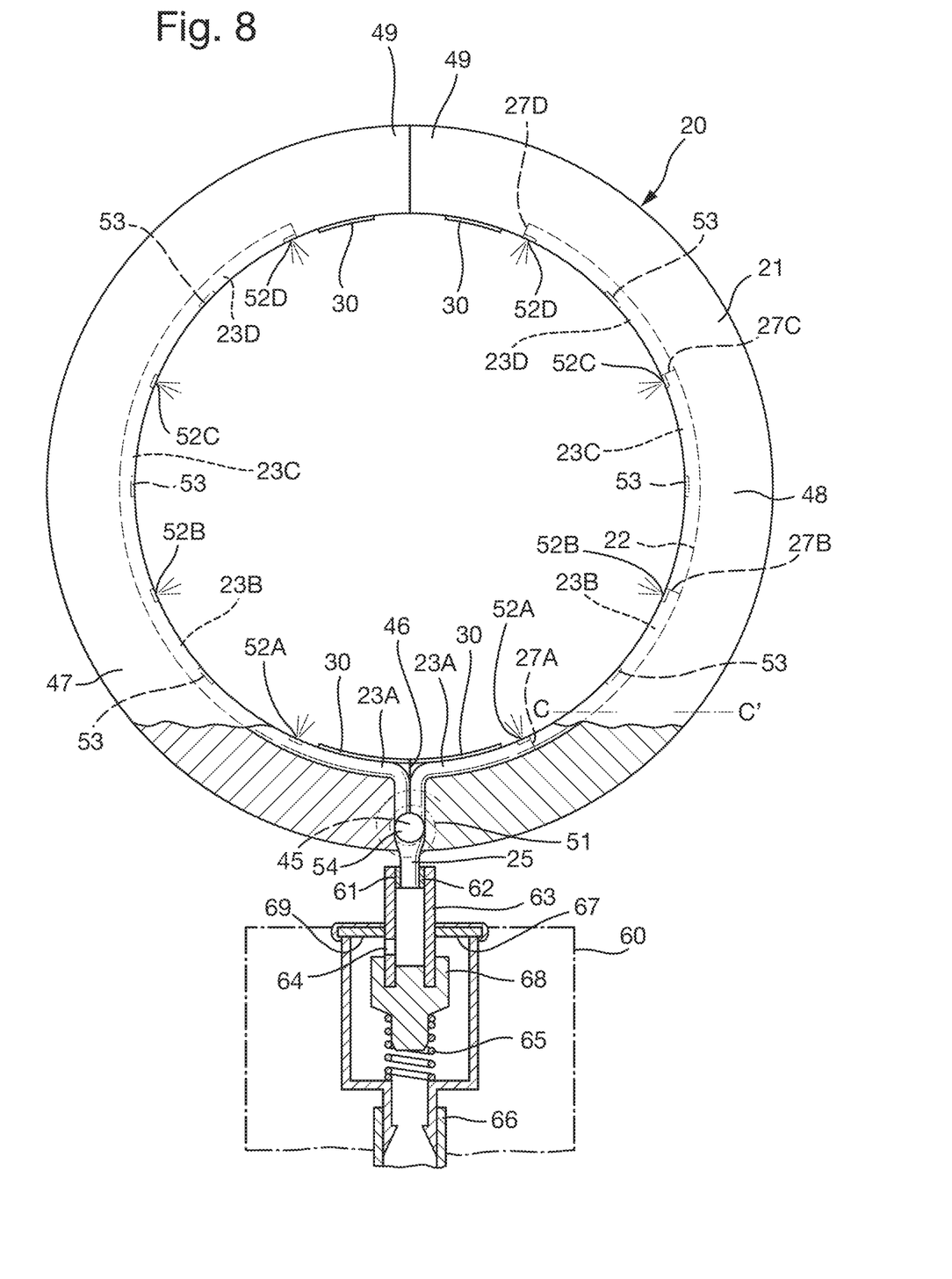
FIG. 8 shows a dispenser similar to that of FIG. 6 but with treatment supplied directly from a pressurised container.

Such an arrangement is shown in FIG. 8.

In FIG. 8, a dispenser 20 comprises two semi-circular arms 47 and 48 (as in FIGS. 6 and 7) pivoted at pivot 45 together at their lower proximal ends, and in the closed position butting against one another at their distal ends 49. Optionally there is a spring 51 associated with the pivot 45, urging the arms to close together at the distal ends 49. As shown in FIG. 8, when closed together the two semi-circular arms 47 and 48 form a hoop 21, however the two arms 47 and 48 could take up the form of a C or U shape rather than a hoop.

A plurality of tubes, 23A, 23B, 23C, 23D, connect a manifold 25 at the proximal ends of the arms 47 and 48 to nozzles 52A, 52B, 52C 52D distributed around the inside of the arms 47 and 48 and located at the ends 27A, 27B, 27C, 27D of the tubes 23A, 23B, 23C, 23D. Self-sealing slits could replace the nozzles 52A, 52B, 52C and 52D. The tubes 23A, 23B 23C and 23D are mounted in grooves 22 in the inner surfaces of the arms 47 and 48. Each individual tube 23A, 23B, 23C 23D connects an individual a nozzle 52A, 52B, 52C and 52D to the manifold 25 as in FIG. 8. In this way, the fluid pressure at each nozzle is substantially the same; the flow rate of the fluid from one aperture is substantially the same as that from another aperture.

As In the arrangement of FIGS. 6 and 7, the arms 47 and 48 can be opened and a body part inserted between their distal ends 49. The orifice 61 of a container 60 containing the treatment and gas under pressure is connected to the manifold 25, an O-ring 62 sealing between the manifold and the orifice. The container 60 is of conventional design for a pressurised fluid dispensing container. When the dispenser 20 and patient are ready, the actuator 63 is depressed against a plug 68 and spring 65 opening an aperture 64 releasing the treatment rising up dip tube 66 from near the bottom of the container under pressure through the manifold 25, into tubes 23A, 23B, 23C and 23D and our of nozzles 52A, 52B 52C and 52D, spraying onto a body part contained within the dispenser.

Once treatment is complete, downward pressure on the dispenser 20 is released; spring 65 urges plug 68 upwards (as seen in the drawing) against a gasket 69 at the top of the container 60 closing the aperture 64, and thus stopping the flow of treatment.

In FIG. 8, the pivoted arms 47 and 48 can be replaced with a fixed hoop as illustrated in FIGS. 4 to 7. Likewise the four tubes 23A, 23B 23C 23D can be replaced with single tubes 23 in each side of hoop as shown in FIGS. 2 to 5.

There may be some drop in the pressure as the container is depleted in the tubes 23 or 23A, 23B, 23C, 23D, but this may not be critical in all cases. If the drop is critical then a pump arrangement as in FIGS. 2 to 7 should be retained or the container replaced.

Although developed for application to humans, there is no reason in principle why the apparatus should not be used to treat other animals in a similar way.

It can be seen that the device is easy to use for arthritis and other sufferers with limited movement—they simply slip in the finger, wrist etc. into the hoop and a measured dose of pain killer or anti-arthritis treatment is administered via the skin.

In the examples, apertures in the form of both nozzles and self-sealing slit have been described. It would also be possible to use apertures in the form of holes in hoop 5 and tubes 23, although these may be prone to leakage. In the tubes 23 nozzles can be used instead of the self-sealing slits, similarly in hoop 5 self-sealing slits could be used instead of nozzles.

Examples of applications of the device include spray treatments of arthritis, burns, venous ulcers, chronic wounds/infections, eczema and other exfoliating conditions, and in trauma, eradication of MRSA from patients and ward staff/visitors, and disinfection. It can also be used for spray on wound sealing and dressings. One particular use is in the treatment or application of temporary spray-on dressings to patients in emergency evacuations.

The device of the invention can also be used for non-medical purposes such as treatments applying perfumes, sun tan lotions, soaps and the like to parts of the body.

The range of products that may be applied using the device includes, disinfectant/cleaning agents (such as iodine), medicinal agents (e.g. coagulants, repair stimulants, antibiotics, analgesics, anti-inflammatory agents), protective layers (to protect wound from air/infection/abrasion, to prevent loss of body fluids and loss of drugs), Immobilisers (e.g. plaster or polymer).

Although developed for spraying fluids treatments and drugs onto human body parts, there is no reason in principle why the apparatus should not be used to spray treatments and drugs as fluids onto parts of animals in a similar way.

The invention claimed is:

1. A drug or medical treatment dispenser for application of a drug or medical treatment in a fluid to a body part, the dispenser comprising:
a hoop or a pair of pivoted together semi-circular arms configured to at least partially surround the body part and comprising at least one groove and at least one tube inset in the groove(s);
the tube(s) comprising one or more apertures directed towards a center of the hoop or of the semi-circular arms, from which aperture(s) the drug or treatment in the fluid may be sprayed onto the body part placed in the hoop or the semi-circular arms of the dispenser;
a pump comprising an inlet and an outlet;
a manifold through which the aperture(s) are connected by the tube(s) to the outlet of the pump;
a container configured to contain the drug or medical treatment and connected to the inlet of the pump.

2. The drug or medical treatment dispenser according to claim 1, in which the device comprises a wand configured to pass over the body part.

3. The drug or medical treatment dispenser according to claim 1, in which the aperture(s) comprise nozzles or self-sealing slits.

4. The drug or medical treatment dispenser according to claim 1, further comprising a sensor configured to sense presence of the body part in the dispenser, the sensor further configured to activate spraying of the drug or medical treatment through the aperture(s) when the body part is sensed by the sensor.

5. The drug or medical treatment dispenser according to claim 1, further comprising a sensor configured to identify that the body part inserted is a specified body part of a specified person and configured to prevent activation unless the specified body part of the specified person is inserted.

6. The drug or medical treatment dispenser according to claim 1, wherein fluid flows from one aperture at a same rate as fluid flows from another aperture located further away from the pump.

7. The drug or medical treatment dispenser according to claim 6, further comprising a sensor connected to a programmable chip, the dispenser comprising at least two tubes, said sensor and chip being configured in combination to make an identification of presence of the body part in the dispenser, the programmable chip being configured to control opening and closing of valves allowing or preventing entry of the fluid into one or more of the tubes in response to the identification.

8. The drug or medical treatment dispenser according to claim 1, further comprising a sensor, and wherein the pump is configured to operate only when a correct body part is identified by the sensor.

9. The drug or medical treatment dispenser according to claim 1 in which the pair of pivoted together semi-circular arms form a hoop, a C shape, or a U shape around a body part when the arms are moved towards one another.

10. The drug or medical treatment dispenser according to claim 9, further comprising a spring configured to urge the arms towards one another.

11. The drug or medical treatment dispenser according to claim 6, in which the apertures are of increasing size to compensate for pressure drop as distance of the apertures from the pump increases.

12. The drug or medical treatment dispenser according to claim 6, in which the tube(s) are of a changing diameter to compensate for pressure drop as distance from the pump increases.

13. The drug or medical treatment dispenser according to claim 1, in which each individual aperture is connected by a separate tube to the manifold.

14. The drug or medical treatment dispenser according to claim 13, in which the tubes are of different diameters.

* * * * *